United States Patent [19]
Young et al.

[11] Patent Number: 6,075,024
[45] Date of Patent: Jun. 13, 2000

[54] METHODS FOR TREATING INFECTION USING OPTICALLY PURE (S)-LOMEFLOXACIN

[75] Inventors: James W. Young, Palo Alto, Calif.; A. K. Gunnar Aberg, Westborough, Mass.

[73] Assignee: Sepracor Inc., Marlborough, Mass.

[21] Appl. No.: 08/455,471

[22] Filed: May 31, 1995

Related U.S. Application Data

[63] Continuation-in-part of application No. 08/285,610, Aug. 3, 1994, abandoned, which is a continuation of application No. 07/981,469, Nov. 25, 1992, abandoned, which is a continuation-in-part of application No. 07/799,243, Nov. 27, 1991, abandoned.

[51] Int. Cl.[7] .......................... A61K 31/495; A61K 31/50
[52] U.S. Cl. ............................................................ 514/254
[58] Field of Search ............................................. 514/254

[56] References Cited

U.S. PATENT DOCUMENTS

| | | | |
|---|---|---|---|
| 4,528,287 | 7/1985 | Itoh et al. | 514/254 |
| 4,992,445 | 2/1991 | Lawter et al. | 514/279 |
| 5,476,854 | 12/1995 | Young | 514/254 |

FOREIGN PATENT DOCUMENTS

| | | | |
|---|---|---|---|
| 0 294 601 A2 | 12/1988 | European Pat. Off. | |
| 3433924 A1 | 4/1985 | Germany | A61K 31/495 |
| 61-85381 | 4/1986 | Japan . | |
| WO 91/09616 | 7/1991 | WIPO | A61K 31/495 |
| WO 93/10785 | 6/1993 | WIPO | A61K 37/22 |
| WO 93/10786 | 6/1993 | WIPO | A61K 31/495 |

OTHER PUBLICATIONS

Banerjee, D.K., et al., "In–Vitro Activity of Lomefloxacin Against Pathogenic and Environmental Mycobacteria," *J. Antimicrob. Chemother.*, 30(2):236–238 (1992).
Gelber, R.H., et al., "Activities of Various Quinolone Antibiotics Against *Mycobacterium leprae* in Infected Mice," *Antimicrob. Agents Chemother.*, 36(11):2544–2547 (1992).
Kawahara, S., et al., "In vitro Activities of Newly Developed Quinolones, Fleroxacin, Lomefloxacin, and Sparfloxacin Against Mycobacterium Tuberculosis," Questel, MEDLINE, Accession No. 92046949, 66(6):429–431 (1991).
Pattyn, S.R., "Anti–Mycobacterium Leprae Activity of Several Quinolones Studies in the Mouse," *Int. J. Lepr. & Other Mycobact. Dis.*, 59(4):613–617 (1991).
Inderlied, C.B., et al., "In Vitro Activity of Lomefloxacin as Compared with Ciprofloxacin," *Diagn. Microbiol. Infect. Dis.*, 12(3):17s–20s (1989).
Bianchini, H.N., et al., "A Ten–Laboratory Study of Lomefloxacin (NY–198 or SC 47111) Antimicrobial Activity in Argentina," *Digan. Microbiol. Infect. Dis.*, 12(3):45s–50s (1989).
Blum, R.A., "Influence of Renal Function on the Pharmacokinetics of Lomefloxacin Compared With Other Fluoroquinolones", *The American Journal of Medicine* 92(4A): 18S–21S (1992).

Cox, C.E., "A Comparison of the Safety and Efficacy of Lomefloxacin and Ciprofloxacin in the Treatment of Complicated or Recurrent Urinary Tract Infections", *The American Journal of Medicine* 92(4A): 82S–86S (1992).
Felmingham, D. and Robbins, M.J., "In vitro Activity of Lomefloxacin and Other Antimicrobials Against Bacterial Enteritis Pathogens", *Diagn. Microbiol. Infect. Dis.* 15: 339–343 (1992).
Iravani, A., "Efficacy of Lomefloxacin as Compared to Norfloxacin in the Treatment of Uncomplicated Urinary Tract Infections in Adults", *The American Journal of Medicine* 92(4A): 75S–81S (1992).
Lebrec, D., "Pharmacokinetics of Lomefloxacin in Patients with Cirrhosis", *The American Journal of Medicine* 92(4A): 41S–44S (1992).
Nilsen, O.G., "Single–Dose Pharmacokinetics of Lomefloxacin in Patients with Normal and Impaired Renal Function", *The American Journal of Medicine* 92(4A): 38S–40S (1992).
Paton, J. and Reeves, D., "Clinical Features and Management of Adverse Effects of Quinolone Antibacterials", *Drug Safety* 6(1): 8–27 (1991).
Christ, W., "Central Nervous System Toxicity of Quinolones: Human and Animal Findings", *Journal of Antimicrobial Chemotherapy* 26, Suppl. B.: 219–225 (1990).
Morse, I., "Pharmacokinetics and Safety of Single Oral Doses of Lomefloxacin", *Biopharmaceutics & Drug Disposition* vol. II: 543–551 (1990).
Neu, H.C., "Use of Fluoroquinolone Antimicrobial Agents by Cardiovascular and Cardiopulmonary Surgeons", *Texas Heart Institute Journal* 17(1): 12–21 (1990).
Okamoto, Y. et al., "Optical resolution of dihydropyridine enantiomers by High–performance liquid chromatography using phenylcarbamates of polysaccharides as a chiral stationary phase", *Journal of Chromatography* 513: 375–378 (1990).
Scripp's New Product Report, "Lomefloxacin", PJB Publications Ltd., Nov. 1990.
Soons, P.A. et al., "Enantioselective determination of felodipine and other chiral dihydropyridine calcium entry blockers in human plasma", *Journal of Chromatography* 528: 343–356 (1990).
Wagai, N. et al., "Phototoxic potential of quinolone antibacterial agents in Balb/c mice", *Toxicology Letters* 54: 299–308 (1990).
Hunt, T.L. and Adams, M.A., "Pharmacokinetics and Safety of Lomefloxacin Following Multiple Doses", *Diagn. Microbiol. Infect. Dis.* 12: 181–187 (1989).

(List continued on next page.)

*Primary Examiner*—Russell Travers
*Attorney, Agent, or Firm*—Pennie & Edmonds LLP

[57] ABSTRACT

Methods and compositions are disclosed utilizing the optically pure (S)-isomer of lomefloxacin to treat bacterial infection. In particular, this compound is a potent drug for the treatment of Mycobacteria infection.

10 Claims, No Drawings

OTHER PUBLICATIONS

Magalhaes, M. et al., "Lomefloxacin Activity Against 2,813 Clinical Isolates: A Collaborative Study at Three Medical Centers in Brazil", 12: 35S–39S (1989).

Simor, A.E. et al., "Comparative In Vitro Activities of Six New Fluorozuinolones and Other Oral Antimicrobial Agents against *Campylobacter pylori*", *Antimicrobial Agents and Chemotherapy* 33(1): 108–109 (1989).

Siporin, C., "The Evolution of Fluorinated Quinolones: Pharmacology, Microbiological Activity, Clinical Uses, and Toxicities", *Annu. Rev. Microbiol.* 43: 601–27 (1989).

Hardy, D.J. et al., "Susceptibility of *Campylobacter pylori* to macrolides and fluoroquinolones", *Journal of Antimicrobial Chemotherapy* 22: 631–636 (1988).

Hupertz, V. et al., "Susceptibility of *Campylobacter pylori* Isolated from Pediatric and Adult Patients to Seven New Quinolone Antibiotics and Nalidixic Acid", *Chemotherapy* 34: 341–344 (1988).

Une, T. et al., "In Vitro Activity of DR–3355, an Optically Active Ofloxacin", *Antimicrobial Agents and Chemotherapy* 32(9): 1336–1340 (1988).

Von Rosenstiel, N. et al., "Quinolone Antibacterials", *Drugs* 47(6):872–901 (1994).

Wadworth, A. et al., "Lomefloxacin", *Drugs* 46(6):1018–1060 (1991).

Piersimoni, C. et al., "In Vitro Activity of the New Quinolone Lomefloxacin against *Mycobacterium tuberculosis*", *Am. Rev. Respir. Dis.* 146:1445–1447 (1992).

METHODS FOR TREATING INFECTION USING OPTICALLY PURE (S)-LOMEFLOXACIN

This is a continuation-in-part application of U.S. patent application Ser. No. 08/285,610, filed Aug. 3, 1994, now abandoned, which is a continuation of application Ser. No. 07/981,469, filed Nov. 25, 1992, now abandoned, which is a continuation-in-part of application Ser. No. 07/799,243, filed Nov. 27, 1991, now abandoned, each of which is incorporated by reference in its entirety.

1. FIELD OF THE INVENTION

This invention relates to novel compositions of matter containing optically pure (S)-lomefloxacin. These compositions possess potent activity in treating various infections while avoiding adverse effects associated with racemic lomefloxacin including but not limited to headache, stomach discomfort, gastrointestinal disorders, hypoglycemia, renal and hepatic dysfunction, allergic reactions and respiratory distress, and arthropathy, such as cartilage lesions and erosion and abnormalities in bone growth in immature patients. Additionally, these novel compositions of matter containing optically pure (S)-lomefloxacin are useful in treating infection in those patients with impaired renal function. Also disclosed are methods for treating the above-described conditions in a human while avoiding adverse effects that are associated with the racemic mixture of lomefloxacin, by administering the (S)-isomer of lomefloxacin to said human.

2. BACKGROUND OF THE INVENTION

2.1. Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric mixture. A 50:50 mixture of enantiomers is referred to as a racemic mixture.

Stereochemical purity is of importance in the field of pharmaceuticals, where 12 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, and that the corresponding L-enantiomer was a potent teratogen.

2.2. Racemic Lomefloxacin

Lomefloxacin is described in U.S. Pat. No. 4,528,287 and Japan Patent Publication No. 64979 (1985). Lomefloxacin is currently available commercially in the United States as MAXAQUIN® as well as in Argentina, Japan, Mexico and certain countries in Asia and Eastern Europe, as the racemic mixture, i.e., it is a 1:1 mixture of optical isomers. It is the optically pure, or substantially optically pure (S)-isomer of lomefloxacin, which is the subject of the present invention, hereinafter referred to as (S)-lomefloxacin.

Racemic lomefloxacin, having the chemical name 1-ethyl-6,8-difluoro-1,4-dihydro-7-(3-methyl-lpiperazinyl)-4-oxo- 3-quinolinecarboxylic acid, belongs to the quinoline class of antibiotics. The quinoline antibiotics, in general, exhibit a broad spectrum of antibacterial action, demonstrating effectiveness against both Gram-positive and Gram-negative bacterial strains. Quinoline antibiotics have been shown to be effective in treating infections of the respiratory, genito-urinary, and gastrointestinal tracts. They have also demonstrated utility in the treatment of patients with cystic fibrosis and pulmonary infections. Effectiveness has also been demonstrated in the treatment of intra-abdominal, bone and joint, skin, soft-tissue, pelvic, and eye, ear, nose, and throat infections.

Examples of Gram-positive bacteria include but are not limited to Streptococcus, Staphlococcus, Mycobacteria, Listeriaceae, Bacillus and Nocardia. A number of Gram-positive bacteria cause respiratory tract infections including, but not limited to, *Streptococcus pneumoniae* and Mycobacteria. The majority of clinically diagnosed cases of pneumonia are caused by *Streptococcus pneumoniae*. However, recently there has been an increase in the number of pneumonias caused by Mycobacteria. Three different species of Mycobacteria, *Mycobacteria tuberculosis* (*M. tuberculosis*), *Mycobacteria bovis* (*M. bovis*), and *Mycobacteria africanum* (*M. africanum*) can cause a disease state commonly known as tuberculosis. Tuberculosis is a highly contagious disease which is most commonly transmitted by aerosolized respiratory secretions. While infection usually begins in the lungs, mycobacteria can easily spread to other organs as well, including eyes, intestine, pericardium, peritoneum, bone and joints, urinary tract, and lymphatic system. See The Merck Manual, 16th ed., pp. 131–146, Merck Sharpe & Dohme.

In addition to *M. tuberculosis, M. bovis,* and *M. africanum,* other species of Mycobacteria include *M. chelonei, M. Marinum, M. avium* and *M. kansasii.*

The quinoline antibiotics derive their activity through inhibition of the bacterial enzyme, DNA gyrase, which is responsible for catalyzing the bacterial DNA supercoiling necessary to pack DNA filaments into bacterial cells. This inhibition causes irreversible chromosome damage leading to bacterial cell death. The selectivity of quinoline antibiotics for bacterial cells is the result of the supercoiling mechanism in eukariotic cells being mediated by a different set of enzymes not susceptible to quinoline inhibition. Quinoline antibiotics are also thought to interfere with proper bacterial cell membrane function, also contributing to cell death.

The first quinoline antibiotic to be commercialized, nalidixic acid, was discovered following the observation that the structurally similar 6-chloro-1H-ethyl-4-oxoquinolone-3-carboxylic acid, a minor by-product of the commercial production of the antimalarial agent chloroquine, exhibited weak antibacterial action. Since the discovery of nalidixic acid, some 7,000 analogues belonging to approximately 16 different ring systems have been synthesized and tested for antibacterial action. From this data, a comprehensive structure/activity relationship has been elucidated.

Structural activity studies have demonstrated that substitution,at position 1 and a carbonyl substitution at position 4 on the quinoline ring appear to be required for antimicrobial activity. No substitution at position 2 and a carboxyl function at position 3 also appear to be required for activity. The only exception appears to be a thiazolidone ring fused at positions 2 and 3. Depending on modification, the presence of additional fused rings, as well as various ring substitutions can be either beneficial or detrimental to activity.

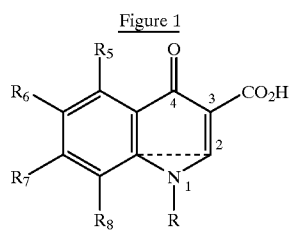

Figure 1

Racemic lomefloxacin exhibits a broad spectrum of antibacterial action, demonstrating effectiveness against both Gram-positive and Gram-negative bacterial strains. Lomefloxacin has shown to be more effective against Gram-negative bacteria. In particular, lomefloxacin has shown excellent bacteriocidal activity against strains of Enterobacteriaceae, *Haemophilus influenzas, Neisseria gonorrhoeae, Branhamella catarrhalis, L. pneumophilia*, and good-to-moderate activity against strains of Acinetobacter, *Pseudomonas aeruginosa, Staphylococcus aureus* and *Staphylococcus epidermidis*, but poor activity against *Pseudomonas cepacia*. There is only a low propensity for bacteria to develop a resistance to lomefloxacin by spontaneous mutation. However, development of resistance is facilitated when bacteria are exposed to sub-inhibitory concentrations of the antibiotic.

Lomefloxacin has an average elimination half-life of approximately 8 hours with peak plasma concentrations occurring at approximately 1 hour after oral dosing in humans. Its long half-life and dose proportionality have lead to introduction of lomefloxacin as the first, once-daily 4-quinoline antibiotic.

Furthermore, unlike ciprofloxacin, lomefloxacin does not interfere with the metabolism of theophylline. Likewise, co-administration of ranitidine with lomefloxacin has no effect on lomefloxacin's pharmacokinetics. However, coadministration of sucralfate with lomefloxacin, presumably through aluminum complexation, does reduce the absorption of the antibiotic. In patients with reduced renal function, lomefloxacin exhibits reduced renal clearance, with a consequential prolongation of the half-life by up to 24 hours. Antibacterial levels of lomefloxacin are therefore maintained in patients with reduced renal function for up to five days.

Little is known about the pharmacology of the individual isomers of lomefloxacin. The pure enantiomer form of ofloxacin, a related quinoline antibiotic, has been studied (Antimicrob. Agents Chemother., 1988, 32(9), 1336–1340). The (S)-isomer of ofloxacin has been reported to be twice as potent a bactericide as the racemate against a variety of Gram-positive and Gram-negative pathogens.

The racemic mixture of lomefloxacin is presently used primarily as an antibiotic agent for treatment of infection of the upper respiratory and urinary tracts. Viral infections of the respiratory tract are acute illnesses with local and systemic manifestations. Coryza (common cold), pharyngitis, laryngitis (including croup), and tracheobronchitis are common respiratory syndromes. See, for example, Merck Manual 5th Ed., p. 169, Merck, Sharpe & Dohme Research Laboratories (1987). Bacterial infections of the lower urinary tract are very common. The majority of urinary tract infections are caused by Gram-negative bacteria. Organisms gaining access to the urethra may colonize on the periurethral glands and produce acute and chronic infection. This condition is termed urethritis. Infections of the prostate gland give rise to the condition prostatitis. Enteric, Gram-negative organisms are the most common cause of prostate infection. Merck Manual 5th Ed., p. 1610, Merck, Sharpe & Dohme Research Laboratories (1987).

Additionally, racemic lomefloxacin has also been used in treating enteritis, sexually transmitted diseases, obstetric and gynecological infections, surgical infections, skin, soft tissue and joint infections, otorhinolaryngologic infections and ophthalmological infections.

Lomefloxacin has been shown to have activity against Mycobacteria tuberculosis, the most common causative agent of the tuberculosis disease. (Piersimoni et al., 1992, "In Vitro Activity of the New Quinolone Lomefloxacin against *Mycobacterium tuberculosis*," Am. Rev. Respir. Dis. 146:1445–1447). Piersimoni et al. compared the inhibitory effect of ofloxacin, ciprofloxacin, and lomefloxacin against 79 strains of *M. tuberculosis* which were susceptible to conventional drug therapy and 11 strains of *M. tuberculosis* which were resistant to conventional drug therapy. Their data showed that the MIC50 and MIC90 of lomefloxacin in the 79 susceptible strains were, respectively, 0.96 $\mu$g/ml and 1.02 $\mu$g/ml with a range of 0.5 to 2.0 $\mu$g/ml. The MIC50 and MIC90 of lomefloxacin in the 11 resistant strains were, respectively, 1.0 $\mu$g/ml and 1.1 $\mu$g/ml. Piersomoni et al. concluded that lomefloxacin, orally administered once daily could achieve adequate serum levels to inhibit *M. tuberculosis*.

Although lomefloxacin and quinoline antibiotics have several advantages, they also have disadvantages, namely, adverse effects. The adverse effects of quinoline antibiotics in general include arthropathy, headache, stomach discomfort, gastrointestinal disorders, hypoglycemia, renal and hepatic dysfunction, allergic reactions and respiratory distress, and central nervous system effects including convulsions, increased intracranial pressure, and toxic psychoses. The adverse effects of lomefloxacin, in particular, include but are not limited to headache, stomach discomfort, gastrointestinal disorders, dizziness, phototoxicity, and arthropathy, such as cartilage lesions and erosion and abnormalities in bone growth in immature patients. Thus, it would be particularly desirable to find a compound with the advantages of the racemic mixture of lomefloxacin which would not have the aforementioned disadvantages.

3. SUMMARY OF THE INVENTION

It has now been discovered that the optically pure (S)-isomer of lomefloxacin is effective in treating infection in a human. Further, it has also been discovered that the optically pure (S)-isomer of lomefloxacin is effective in treating infection in a human while avoiding adverse effects associated with the administration of racemic lomefloxacin, including but not limited to headache, stomach discomfort, gastrointestinal disorders, hypoglycemia, renal and hepatic dysfunction, allergic reactions and respiratory distress, and arthropathy, such as cartilage lesions and erosion and abnormalities in bone growth in immature patients. The present invention also includes methods for treating the above-described conditions in a human while avoiding the adverse effects that are associated with the racemic mixture of lomefloxacin, by administering the optically pure (S)-isomer of lomefloxacin to said human.

4. DETAILED DESCRIPTION OF THE INVENTION

The present invention is a method of treating infection in a human which comprises administering to the human, an amount of (S)-lomefloxacin, or a pharmaceutically acceptable thereof, substantially free of its (R)-stereoisomer, said amount being sufficient to alleviate infection.

The present invention encompasses a method of treating infection in a human while avoiding the concomitant liability of adverse effects associated with the administration of racemic lomefloxacin, which comprises administering to said human, an amount of (S)-lomefloxacin, or a pharmaceutically acceptable salt thereof, substantially free of its (R)stereoisomer, said amount being sufficient to alleviate infection, but insufficient to cause said adverse effects associated with administration of racemic lomefloxacin.

The present invention also encompasses an antibiotic composition for treating infection in a human which comprises, an amount of (S)-lomefloxacin or a pharmaceutically acceptable salt thereof, substantially free of its (R)-stereoisomer, said amount being sufficient to alleviate said infection but insufficient to cause adverse effects associated with lomefloxacin.

The available racemic mixture of lomefloxacin (i.e., a 1:1 mixture of the two enantiomers) possesses antibiotic activity, and provides therapy and a reduction of symptoms in a variety of conditions and disorders related to bacterial infection; however, this racemic mixture, while offering the expectation of efficacy, causes adverse effects. Utilizing the substantially optically pure (S)-isomer of lomefloxacin results in clearer dose-related definitions of efficacy, diminished adverse effects, and accordingly, an improved therapeutic index. It is therefore, more desirable to use the (S)-isomer of lomefloxacin.

The term "adverse effects" includes, but is not limited to headache, stomach discomfort, gastrointestinal disorders, hypoglycemia, renal and hepatic dysfunction, allergic reactions, nausea, photosensitivity (phototoxicity), dizziness, diarrhea, respiratory distress, and arthropathy, such as cartilage lesions and erosion and abnormalities in bone growth in immature patients. (See Physician's Desk Reference, 1994, p. 2216.)

The term "substantially free of its (R)-stereoisomer" as used herein means that the composition contains a greater proportion of the (S)-isomer of lomefloxacin in relation to the (R)-isomer of lomefloxacin. In a preferred embodiment the term "substantially free of its (R)-isomer" as used herein means that the composition contains at least 90% by weight of (S)-lomefloxacin, and 10% by weight or less of (R)-lomefloxacin. These percentages are based on the total amount of lomefloxacin present in the composition. In the most preferred embodiment the term "substantially free of the (R)-stereoisomer" means that the composition contains at least 99% by weight (S)-lomefloxacin, and 1% or less of (R)lomefloxacin. In another preferred embodiment, the term "substantially free of its (R)-stereoisomer" as used herein means that the composition contains 100% by weight of (S)-lomefloxacin. The terms "substantially optically pure (S)-isomer of lomefloxacin" and "optically pure (S)-isomer of lomefloxacin" are also encompassed by the above-described amounts.

The term "amount sufficient to alleviate infection" as used herein means an amount which eliminates or inhibits the growth of foreign microorganisms that are harmful to the normal functioning of the host organism, particularly humans.

It has unexpectedly been discovered that (S)-lomefloxacin is more active than (R,S)- or (R)- lomefloxacin in inhibiting certain species of Mycobacteria, including but not limited to M. tuberculosis, M. chelonel and M. marinum. It has further been discovered that (S)-lomefloxacin is more active than (R)- lomefloxacin in inhibiting M. avium and M. kansasii.

In a specific embodiment of the present invention, an effective amount of (S)-lomefloxacin is used to treat an individual infected with Mycobacteria; said effective amount being sufficient to reduce the infection. In an preferred embodiment, the Mycobacteria is selected from a group consisting of M. tuberculosis, M. chelonel, M. marinum, M. avium and M. kansasii.

Thus, the present invention encompasses an improved method of treating infection in a human or animal, caused by mycobacteria which comprises administering an effective amount of S-lomefloxacin, substantially free of its R-stereoisomer. In addition, the invention encompasses the treatment of mycobacteria infection in a human by administering an effective amount of S-lomefloxacin, substantially free of its R-stereoisomer alone or in combination with another therapeutic agent, such as an antiviral or another antibiotic. Suitable antivirals or antibiotics are known to those skilled in the art and include but are not limited to AZT, acyclovir, gancyclovir, ribavarin; and penicillin, cephalixm, amikacin, gentamycin, ethanbutil, rifampacin, erythromycin, and tetracycline.

As a result of the increased activity of S-lomefloxacin over that of the racemate or R-lomefloxacin in the treatment of certain bacterial infections, the effective dose may be lower than the doses described herein, e.g., from about 50 mg to 400 mg per day; preferably 50 mg to 200 mg per day. However, the doses described further herein may also be used if desired or necessary for a particular patient.

The chemical synthesis of the racemic mixture of lomefloxacin can be performed by the method described in U.S. Pat. No. 4,528,287. The method involves the reaction of 1,4-dihydro-4oxoquinoline-3-carboxylic acid 2 (where X=Cl or F) with piperazine 1. The preparation of the type 2 compounds has previously been described in Japanese Patent Publication No. 141286/1978, Japanese Patent Publication No. 47658/1980 and Japanese Patent Publication No. 30964/1981.

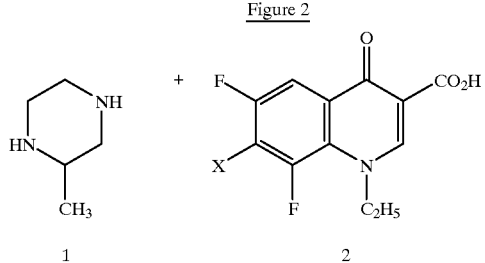

Figure 2

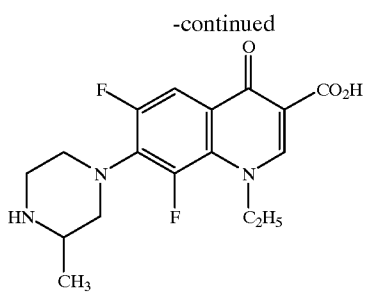

Furthermore, the (S)-isomer of lomefloxacin may be obtained by resolution of the mixture of enantiomers of lomefloxacin using conventional means such as an optically active resolving acid; see, for example "Stereochemistry of Carbon Compounds," by D. L. Eliel (McGraw Hill 1962) and Lochmuller, C. H. et al., *J. Chromatogr.* 113:(3) 283–302 (1975). (S)-Lomefloxacin can be prepared from the racemate through the diastereomeric crystallization scheme shown below:

Racemic lomefloxacin is treated with an optically pure base (an amine is shown above) to give a pair of diastereomeric salts. The difference in solubility between the two diastereomers allows one to be selectively crystallized from the solvent while the other remains in solution. Crystals of the single diastereomer are then separated from the other diastereomer by filtration. Once separated, the diastereomers can be converted back to the original enantiomers by treatment with acid.

The magnitude of a prophylactic or therapeutic dose of (S)-lomefloxacin in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 100 mg to about 400 mg. However, the dosage may be as high as about 800 mg. Preferably, a daily dose range should be between about 100 mg to about 200 mg. In managing the patient, the therapy should be initiated at a lower dose, perhaps about 100 mg to about 200 mg and increased up to about 400 mg or higher

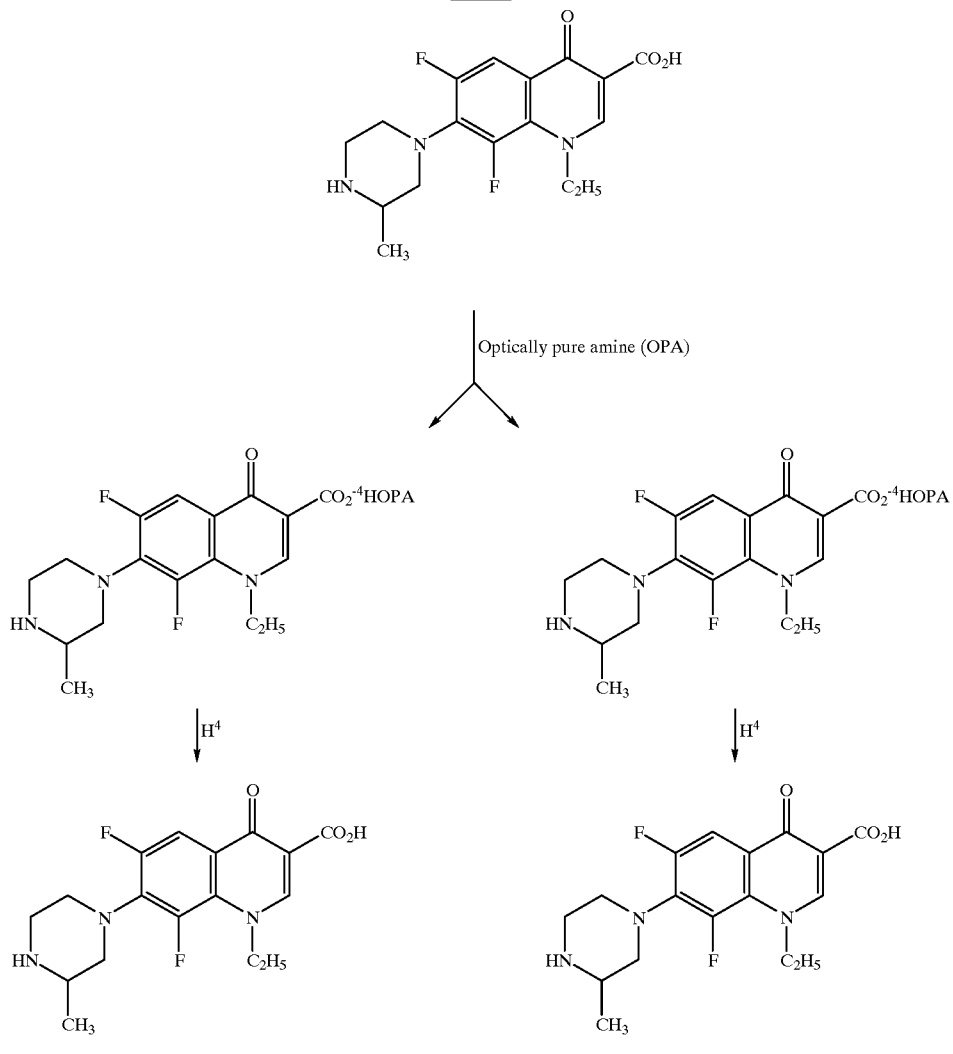

Figure 3 depending on the patient's global response. It is further recommended that children, patients over age 65, and those with impaired renal or hepatic function, initially receive low doses. Those dosages should also be titrated based on global response and blood level. In some cases, it may be necessary to use dosages outside these ranges.

The term, "an amount sufficient to alleviate infection but insufficient to cause said adverse effects," is encompassed by the above described dosage amounts and dose frequency schedule.

The term, "method of treating infection" as used herein, includes but is not limited to infections such as urinary tract infection, upper and lower respiratory tract infection, sexually transmitted infection, ophthalmological infection, gastrointestinal infections such as those caused by *H. pylori* and any other infections which may arise in cells or tissues of a human and which require treatment with antibiotics. Such infection may be caused by either Gram-positive or Gram-negative bacteria. The Gram-negative bacteria include but are not limited to Escherichia, Haemophillus, Klebsiella, Proteus, Moraxella, Citrobacter, Enterobacter, Pseudomonas, Salmonella, Shigella, Yersinia, Camplobacter, Neisseriaceae and Serratia. The Gram-positive bacteria include but are not limited to Staphlococcus, Streptococcus, Bacillus and Mycobacteria.

The present inventors have shown that optically pure (S)-lomefloxacin unexpectedly has an even lower MIC50 and a lower range MIC50 than that for either (R)- or racemic lomefloxacin for *Mycobacteria tuberculosis* and a lower MIC50 than R-lomefloxacin for *Mycobacteria kansasii* and *Mycobacteria avium*. (See infra, Example 6).

Any suitable route of administration may be employed for providing the patient with an effective dosage of (S)-lomefloxacin. For example, oral, rectal, parenteral, transdermal, subcutaneous, intramuscular, and the like may be employed as appropriate. Dosage forms include tablets, coated tablets, troches, dispersions, suspensions, solutions, caplets, capsules, patches, and,the like.

The pharmaceutical compositions of the present invention comprise (S)-lomefloxacin as active ingredient, or a pharmaceutically acceptable salt thereof, and may also contain a pharmaceutically acceptable carrier, and optionally, other therapeutic ingredients. (S)-lomefloxacin hydrochloride is a pharmaceutically acceptable salt of (S)-lomefloxacin. The most preferred pharmaceutically acceptable salt of (S)-lomefloxacin is the monohydrochloride salt.

The term "pharmaceutically acceptable salts" refers to salts prepared from pharmaceutically acceptable non-toxic acids or bases including inorganic acids and bases and organic acids and bases.

Since the compound of the present invention is both basic and acidic, salts may be prepared from pharmaceutically acceptable non-toxic acids or bases including inorganic and organic acids or inorganic and organic bases. Such salts may contain any of the following anions: acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartrate and the like. Particularly preferred are benzensulfonate, hydrobromate, hydrochloride and sulfate. Such salts may also contain the following cations: aluminum, calcium, lithium, magnesium, potassium, sodium, zinc, benzathine, chloroprocaine, choline, diethanolamine, ethylenediamine, meglumine, and procaine.

The compositions include compositions suitable for oral, rectal and parenteral (including subcutaneous, intramuscular, and intravenous) administration, although the most suitable route in any given case will depend on the nature and severity of the condition being treated. The most preferred route of the present invention is the oral route. The compositions may be conveniently presented in unit dosage form, and prepared by any of the methods well known in the art of pharmacy.

In the case where an oral composition is employed, a suitable dosage range for use is, e.g., from about 100 mg to about 400 mg total daily dose, given as a once daily administration in the morning or in divided doses if required. Preferably, a dose of 400 mg is given as a once daily administration. More preferably, a dose range of between about 100 mg to about 200 mg is given as a once daily administration or in divided doses if required. Patients may be upward titrated from below to within this dose range to a satisfactory control of symptoms.

In practical use, (S)-lomefloxacin can be combined as the active ingredient in intimate admixture with a pharmaceutical carrier according to conventional pharmaceutical compounding techniques. The carrier may take a wide variety of forms depending on the form of the preparation desired for administration, e.g., oral or parenteral (including intravenous injections or infusions). In preparing the compositions for oral dosage form any of the usual pharmaceutical media may be employed. Usual pharmaceutical media includes, for example, water, glycols, oils, alcohols, flavoring agents, preservatives, coloring agents, and the like in the case of oral liquid preparations (such as for example, suspensions, solutions, and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets) with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques. The parenteral dosage form can consist of a sterile solution of the active ingredient, either in its free or salt form, in physiological buffer or sterile water.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; 3,630,200; 4,008,719; 4,687,660 and 4,769,207, the disclosures of which are hereby incorporated by reference.

Pharmaceutical compositions of the present invention suitable for oral administration may be presented as discrete units such as capsules, cachets, or tablets, or aerosols sprays, each containing a predetermined amount of the active ingredient, as a powder or granules, or as a solution or a suspension in an aqueous liquid, a non-aqueous liquid, an oil-in-water emulsion, or a water-in oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients.

Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 100 mg to about 200 mg of the active ingredient, and each cachet or capsule contains from about 100 mg to about 200 mg of the active ingredient, (S)-lomefloxacin. Most preferably, the tablet, cachet or capsule contains either one of two dosages, about 100 mg or about 200 mg of the active ingredient.

The invention is further defined by reference to the following examples describing in detail, the preparation of the compound, and the compositions of the present invention. It will be apparent to those skilled in the art, that many modifications, both to materials, and methods, may be practiced without departing from the purpose and interest of this invention.

5. EXAMPLES

5.1. Example 1

ORAL FORMULATION
Capsules:

| Formula | Quantity per Capsule in mg. | |
|---|---|---|
| Active Ingredient (S)-lomefloxacin hydrochloride | 100 | 200 |
| Lactose | 349 | 249 |
| Corn Starch | 50 | 50 |
| Magnesium Stearate | 1.0 | 1.0 |
| Compression Weight | 500 | 500 |

The active ingredient, (S)-lomefloxacin, lactose, and corn starch are blended until uniform. The magnesium stearate is then blended into the resulting powder. The resulting mixture is encapsulated into suitably sized two-piece hard gelatin capsules.

5.2. Example 2

ORAL FORMULATION
Tablets

| Formula | Quantity per Capsule in mg. | |
|---|---|---|
| Active Ingredient (S)-lomefloxacin hydrochloride | 100 | 100 |
| Lactose BP | 309 | 209 |
| Starch BP | 60 | 60 |
| Pregelatinized Maize Starch BP | 30 | 30 |
| Magnesium Stearate | 1 | 1 |
| Compression Weight | 500 | 500 |

The active ingredient is sieved through a suitable sieve and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to lactose or the compression weight and using punches to suit.

5.3 Example 3

INTRAVENOUS FORMULATION

| Formula | Quantity per 100 ml |
|---|---|
| Active Ingredient (S)-lomefloxacin hydrochloride | 20 ml |
| Sterile Water | 100 ml |

Intravenous infusion solutions of (S)-lomefloxacin may also be prepared with Sodium Chloride Injection USP 0.9% or Dextrose Injection USP 5%.

5.4. Example 4

The anti-bacterial activity of (S)-lomefloxacin towards specific microorganisms is assessed by determination of the minimal inhibitory concentration (MIC) of the compound that prevents growth of that microorganism under assay conditions.

Cultures of various Gram-negative and Gram-positive bacteria, including obligate anaerobes, are grown in various standard media suited to the particular microorganism of interest. [See, for example, Sato, K. et al., *Antimicrob. Agents and Chemotherapy*, 22 (4): 548–553 (1982).] Isolates are grown overnight at 37° C. and adjusted to the density of a 0.5 McFarland standard (i.e., about $10^8$ cFu/mL), and then diluted to $10^{-2}$. One loopful of cells (5 $\mu$L) of each diluted culture (approximately 1000 cells) is then inoculated onto 10-mL drug-containing agar layers in Petri dishes using a multi-point inoculator. Following inoculation, agar plates are incubated for 18 hours at 37° C. in air with the exception of the obligate anaerobes, which are incubated in an atmosphere containing 10% $CO_2$. The MIC is defined as the lowest concentration of (S)-lomefloxacin that completely prevents the visible growth of the inoculum on the surface of the (S)-lomefloxacin-containing medium.

Testing for quinolone-induced arthropathy can be accomplished by administering the quinolone at a suitable dose, on a once-daily basis, to 3–4 month old, skeletally immature Beagle dogs, for 1, 2, 5, or 7 days. A placebo is given to a second group of Beagle dogs to act as a control. A scoring technique that includes lesion size and histologic features is used to determine the progression of the lesions.

5.5. Example 5

Test of Hepatotoxicity

Microsomal Preparation

Hepatic microsomes are prepared from human liver. Tissue is thawed and then homogenized in 0.15 M KCl in a Polytron homogenizer. The homogenate is centrifuged and the pellet is resuspended and homogenized in 0.15 M KCl. Aliquots are frozen and stored at −70° C.

Lymphocyte Preparation

Human lymphocytes are aseptically isolated from fresh, heparinized human blood. Blood is diluted with Eagle's minimal essential medium and layered on Ficoll-Paque. The samples are centrifuged, and lymphocytes are then removed from the aqueous-Ficoll interface and suspended in medium (15 Mm 4-(2-hydroxyethyl)-1-piperazine ethane sulfonic acid [HEPES], pH 7.4). The cells are then centrifuged, washed once in the HEPES medium, and resuspended.

Incubation Conditions and Cytotoxic Assay

Cytotoxicity is assessed by the conversion of MTT (3-(4, 5-dimethylthiazol-2-yl)-2,5-diphenyl tetrazolium bromide)

to a purple formazan. The conversion of MTT to dye is done in multiwell plates.

After preparation, hepatic microsomes or lymphocytes are incubated alone or with the test compound in a concentration range from 1 to 400 $\mu$M at 37° C. in a humidified incubator. After incubation, the microsomes/cells are washed with 5% albumin in HEPES buffered medium and resuspended. The microsomes/cells are then incubated at 37° C. in a humidified incubator. After the incubation, 125 $\mu$g of MTT is added to each well. The plates are incubated at 37° C. and centrifuged. After centrifugation, 100 $\mu$L of isopropanol is added and, after incubation, the optical density is determined using an automated plate-reader.

5.6. Example 6

Susceptibility of Pathogenic Mycobacteria to Lomefloxacin (LM) and Its Optically Active Isomers

5.6.1. Introduction

In this study, the in vitro activities of LM, R-LM and S-LM against 31 clinical isolates of pathogenic mycobacteria and 4 control strains were tested and compared.

5.6.2. Methods

LM, R-LM, and S-LM were synthesized at Sepracor Inc. Drugs were dissolved in distilled water and kept in a −70° C. freezer. Clinical isolates were obtained from the blood or sputum of patients with mycobacterial infection. Control strains include H37RV (ATCC 27294), H37Ra (ATCC 25177), M. marinum (ATCC 927) and M. avium 101.

A broth microdilution method was used. An aliquot of a suspension of mycobacteria was inoculated into 7H9 broth at a ratio of 1:20 and incubated overnight or up to two weeks, depending on the species. The cultures were then adjusted to optical density of No. 0.5 McFarland standard. Inocula were prepared in 7H9 broth at PH 6.7 and incubated at 30° C. (M. marinum) or 37° C. (all other species) in ambient atmosphere. The final concentration of mycobacteria in each microplate well was 1×10$^5$ cfu/ml. The range of concentrations of drugs used was: 0.125–32.0 $\mu$g/mL.

MIC's were determined after 4 days (M. chelonei), 7 days (M. avium, M. maritium, M. kansasii) and 14 days (M. tuberculosis) of incubation. The endpoint for susceptibility/resistance was set at 4.0 $\mu$g/ml. Each organism-drug concentration combination was performed in the duplicate and each experiment was repeated three times.

TABLE 1

Susceptibilities of pathogenic mycobacteria to LM, R-LM and S-LM.

| Strains (n) | Susceptibility ($\mu$g/mL) | | |
|---|---|---|---|
| | LM | R-LM | S-LM |
| M. tuberculosis (12) | | | |
| Range | 0.5–2 | 1–4 | 0.25–1 |
| MIC50 | 1 | 2 | 0.5 |
| MIC90 | 2 | 4 | 1 |

TABLE 1-continued

Susceptibilities of pathogenic mycobacteria to LM, R-LM and S-LM.

| Strains (n) | Susceptibility ($\mu$g/mL) | | |
|---|---|---|---|
| | LM | R-LM | S-LM |
| M. avium (11) | | | |
| Range | 4–16 | 4–32 | 2–16 |
| MIC50 | 8 | 16 | 8 |
| MIC90 | 16 | 32 | 16 |
| M. kansasii (10) | | | |
| Range | 1–2 | 2–4 | 1–2 |
| MIC50 | 1 | 2 | 1 |
| MIC90 | 2 | 4 | 2 |
| M. chelonei C315 (1) | | | |
| MIC | 4 | 4 | 2 |
| M. marinum ATCC927 (1) | | | |
| MIC | 4 | 4 | 2 |

5.6.3. Results

This study demonstrates that the MIC90 of LM, R-LM, and S-LM to M. tuberculosis and M. kansasii are all lower than the endpoint for susceptibility (4.0 $\mu$g/ml) and the reported Cmax of LM (Table 1). For M. tuberculosis isolates, S-LM had the lowest MIC90 (1.0 $\mu$g/ml), microbroth method, with the former having the higher MIC result (ICAAC, New Orleans, 1993; Abstract No. 1584).

5.6.4. Conclusions

1. LM and its isomers have significant activity against clinical strains of M. tuberculosis, M. kansasii, M. chelonei C 315 and M. marinum ATCC 9271.

2. The relative antimycobacterial activities against M. tuberculosis are unexpectedly (S)-LM>LM>(R)-LM and against M. kansasii are unexpectedly (S)-LM≈LM>(R)-LM.

3. For M. kansasii, (S)-LM and LM unexpectedly had the same MIC90 of 2.0 $\mu$g/ml, but (R)-LM had an MIC of 4.0 $\mu$g/ml. All three compounds have much higher MIC90 than the susceptibility endpoint for M. avium. For M. chelonei C315 and M. marinum ATCC 927, the MIC50 of both LM and (R)-LM was 4.0 $\mu$g/ml, but that of (S)-LM was 2.0 $\mu$g/ml.

It may be apparent to those skilled in the art that modifications and variations of the present invention are possible in light of the above disclosure. It is understood that such modifications are within the spirit and scope of the invention, which is defined by the appended claims.

What is claimed is:

1. A method of treating a Mycobacteria infection in a human, which comprises administering to said human a therapeutically effective amount of (S)-lomefloxacin, or a pharmaceutically acceptable salt thereof, substantially free of its (R)-stereoisomer.

2. The method of claim 1 wherein said Mycobacteria is selected from the group consisting of M. tuberculosis, M. chelonei, M. marinum, M. avium, and M. kansasii.

3. The method of claim 1 wherein (S)-lomefloxacin is administered by intravenous infusion, transdermal delivery, or orally as a tablet or a capsule.

4. The method of claim 1 wherein the amount administered is from about 50 mg to about 800 mg.

5. The method of claim 4 wherein the amount administered is from about 50 mg to bout 400 mg.

6. The method of claim 5 wherein the amount administered is from about 50 mg to about 200 mg.

7. The method of claim 1 wherein the (S)-lomefloxacin or a pharmaceutically acceptable salt thereof is greater than approximately 90% by weight of the total weight of lomefloxacin.

8. The method of claim 1 wherein the amount of (S)-lomefloxacin or a pharmaceutically acceptable salt thereof, substantially free of its (R)- stereoisomer is administered together with a pharmaceutically acceptable carrier.

9. The method according to claim 3, 4, 5, or 6, wherein (S)-lomefloxacin is administered as a hydrochloride salt.

10. The method of claim 1 wherein said infection is selected from the group consisting of urinary tract infections, upper and lower respiratory tract infections, bone infections, ophthalmological infections, lymph node infections and intestinal infections.

* * * * *